US011136282B2

(12) United States Patent
Collier et al.

(10) Patent No.: US 11,136,282 B2
(45) Date of Patent: Oct. 5, 2021

(54) METHOD FOR PRODUCING 2,3,3,3-TETRAFLUOROPROPENE AND FACILITY FOR IMPLEMENTING SAID METHOD

(71) Applicant: ARKEMA FRANCE, Colombes (FR)

(72) Inventors: Bertrand Collier, Pierre-Benite (FR); Dominique Deur-Bert, Pierre-Benite (FR); Anne Pigamo, Pierre-Benite (FR); Audrey Riehl, Pierre-Benite (FR); Laurent Wendlinger, Pierre-Benite (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 16/973,462

(22) PCT Filed: Jun. 6, 2019

(86) PCT No.: PCT/FR2019/051355
§ 371 (c)(1),
(2) Date: Dec. 9, 2020

(87) PCT Pub. No.: WO2019/239039
PCT Pub. Date: Dec. 19, 2019

(65) Prior Publication Data
US 2021/0253500 A1    Aug. 19, 2021

(30) Foreign Application Priority Data
Jun. 12, 2018   (FR) ......................................  1855107

(51) Int. Cl.
*C07C 17/20*   (2006.01)
*B01J 19/24*   (2006.01)
(Continued)

(52) U.S. Cl.
CPC ............. *C07C 17/206* (2013.01); *B01J 19/00* (2013.01); *B01J 19/0013* (2013.01); *B01J 19/24* (2013.01);
(Continued)

(58) Field of Classification Search
CPC ..... C07C 17/206; C07C 21/18; C07C 17/269; C07C 21/04; B01J 19/24; B01J 19/00;
(Continued)

(56) References Cited

U.S. PATENT DOCUMENTS

2009/0240090 A1   9/2009   Merkel et al.
2016/0347692 A1*  12/2016  Tirtowidjojo ......... C07C 17/206

FOREIGN PATENT DOCUMENTS

EP         3020695 A1    5/2016
WO      2008054781 A1    5/2008
(Continued)

OTHER PUBLICATIONS

ISA/EP; International Search Report and Written Opinion for International Patent Application No. PCT/FR2019/051355, 11 pages.

*Primary Examiner* — Jafar F Parsa
(74) *Attorney, Agent, or Firm* — NK Patent Law

(57) ABSTRACT

The present invention relates to a process for producing 2,3,3,3-tetrafluoropropene, comprising the steps: i) providing a stream A comprising at least one starting compound selected from the group consisting of 2-chloro-3,3,3-trifluoropropene and 2,3-dichloro-1,1,1-trifluoropropane; and ii) in an adiabatic reactor comprising a fixed bed composed of an inlet and an outlet, bringing said stream A into contact, in the presence or absence of a catalyst, with HF in order to produce a stream B comprising 2,3,3,3-tetrafluoropropene, characterized in that the temperature at the inlet of the fixed bed of said adiabatic reactor is between 300° C. and 400° C. and the longitudinal temperature difference between the inlet
(Continued)

of the fixed bed and the outlet of the fixed bed of said reactor is less than 20° C.

10 Claims, 4 Drawing Sheets

(51) Int. Cl.
*C07C 21/04* (2006.01)
*C07C 21/18* (2006.01)
*B01J 19/00* (2006.01)
*C07C 17/269* (2006.01)

(52) U.S. Cl.
CPC .......... *B01J 19/2415* (2013.01); *C07C 17/269* (2013.01); *C07C 21/04* (2013.01); *C07C 21/18* (2013.01); *B01J 2219/00054* (2013.01); *B01J 2219/00063* (2013.01); *B01J 2219/00155* (2013.01)

(58) Field of Classification Search
CPC ................ B01J 19/0013; B01J 19/2415; B01J 2219/00155; B01J 2219/00054; B01J 2219/00063
See application file for complete search history.

(56) References Cited

FOREIGN PATENT DOCUMENTS

| WO | 2009015317 A1 | 1/2009 |
| WO | 2011044522 A2 | 4/2011 |
| WO | 2013088195 A1 | 6/2013 |

* cited by examiner

METHOD FOR PRODUCING 2,3,3,3-TETRAFLUOROPROPENE AND FACILITY FOR IMPLEMENTING SAID METHOD

CROSS-REFERENCE TO RELATED APPLICATIONS

This application is a U.S. National Stage application of International Patent Application No. PCT/FR2019/051355, filed on Jun. 6, 2019, which claims the benefit of French Patent Application No. 1855107, filed on Jun. 12, 2018.

TECHNICAL FIELD OF THE INVENTION

The present invention relates to the production of hydrofluoroolefins, in particular the present invention relates to the production of 2,3,3,3-tetrafluoropropene.

TECHNOLOGICAL BACKGROUND OF THE INVENTION

Halogenated hydrocarbons, in particular fluorinated hydrocarbons, such as hydrofluoroolefins, are compounds having a structure which is useful as functional materials, solvents, refrigerants, blowing agents and monomers for functional polymers or starting materials for such monomers. Hydrofluoroolefins, such as 2,3,3,3-tetrafluoropropene (HFO-1234yf), are attracting attention because they offer a promising behavior as refrigerants having a low global warming potential.

Processes for the production of fluoroolefins are usually carried out in the presence of a starting substance, such as a chlorine-containing alkane or a chlorine-containing alkene, and in the presence of a fluorinating agent, such as hydrogen fluoride. These processes may be performed in the gas phase or in the liquid phase, in the absence or presence of a catalyst. For example, US 2009/0240090 discloses a gas-phase process for the preparation of 2-chloro-3,3,3-trifluoropropene (HCFO-1233xf) from 1,1,1,2,3-pentachloropropane (HCC-240db). The HCFO-1233xf thus produced is converted into 2-chloro-1,1,1,2-tetrafluoropropane (HCFC-244bb) in the liquid phase and then the latter is converted into 2,3,3,3-tetrafluoropropene.

WO 2013/088195 also discloses a process for the preparation of 2,3,3,3-tetrafluoropropene from 1,1,1,2,3-pentachloropropane and/or 1,1,2,2,3-pentachloropropane, comprising the steps: (a) catalytic reaction of 1,1,1,2,3-pentachloropropane and/or 1,1,2,2,3-pentachloropropane with HF to give a reaction mixture comprising HCl, 2-chloro-3,3,3-trifluoropropene, 2,3,3,3-tetrafluoropropene, unreacted HF and possibly 1,1,1,2,2-pentafluoropropane; (b) separating the reaction mixture into a first stream comprising HCl and 2,3,3,3-tetrafluoropropene and a second stream comprising HF, 2-chloro-3,3,3-trifluoropropene and possibly 1,1,1,2,2-pentafluoropropane; (c) catalytic reaction of said second stream to give a reaction mixture comprising 2,3,3,3-tetrafluoropropene, HCl, unreacted 2-chloro-3,3,3-trifluoropropene, unreacted HF and possibly 1,1,1,2,2-pentafluoropropane; and (d) supplying the reaction mixture obtained in step c) directly to step a) without separation.

In processes for producing 2,3,3,3-tetrafluoropropene, the mastering and control of the reaction temperature is an important parameter which makes it possible to achieve the desired reaction kinetics, conversions and selectivities. This is also particularly recommended to avoid thermal decompositions of thermally sensitive compounds which can impact the activity of the catalyst through the formation of coke and thus considerably reduce the service life of the catalyst.

It is known from WO 2008/054781 that one temperature (300-350° C.) promotes formation of 1234yf, 245cb and 1233xf, while a higher temperature (350-450° C.) promotes formation of the isomers 1234ze, 245fa and 1233zd.

It is therefore important to master and control the temperature of the gases at the inlet of the reactors but also to master and control at all points of the catalytic mass, if there is one.

A multitubular reactor is by definition the ideal isothermal reactor for being able to control the reaction temperature and obtaining the most uniform reaction temperature possible since the catalyst is distributed in tubes and a fluid can circulate in the grille around the tubes to either remove reaction heat in the event of an exothermic reaction, or add heat in the event of an endothermic reaction. On the other hand, when large amounts of catalysts have to be used, the production of a multitubular reactor may prove to be impossible because it would take too many tubes and a homogeneous distribution of the gases in each of the tubes then proves to be very difficult to achieve. In addition, the maintenance of large multitubular reactors proves to be much more difficult and expensive; in particular, the catalyst change operations require lengthy immobilization of the reactor, both to drain the spent catalyst and to fill each tube extremely uniformly with new catalyst. This negative aspect will be reinforced when the service life of the catalyst is short.

Consequently, the use of an adiabatic fixed bed reactor is preferred. Nevertheless, this type of reactor does not exhibit heat exchange with an external environment by definition. Indeed, the adiabatic reactor is characterized by a non-homogeneous temperature at any point of the fixed bed and thus, by a temperature gradient that is both radial and longitudinal, due to the reaction heats and thermal losses at the outer walls of the reactor.

Document US 2016/0347692 describes the implementation of a process for the radical production in a homogeneous gas phase of chlorinated or fluorinated propene in an adiabatic flow reactor controlling the turbulence of the streams entering the reactor.

There is nevertheless a need to improve the processes for producing 2,3,3,3-tetrafluoropropene in adiabatic reactors.

SUMMARY OF THE INVENTION

According to a first aspect, the present invention relates to a process for producing 2,3,3,3-tetrafluoropropene, comprising the steps:
i) providing a stream A comprising at least one starting compound selected from the group consisting of 2-chloro-3,3,3-trifluoropropene and 2,3-dichloro-1,1,1-trifluoropropane; and
ii) in an adiabatic reactor comprising a fixed bed composed of an inlet and an outlet, bringing said stream A into contact, in the presence or absence of a catalyst, with HF in order to produce a stream B comprising 2,3,3,3-tetrafluoropropene, characterized in that the temperature at the inlet of the fixed bed of said adiabatic reactor is between 300° C. and 400° C. and the longitudinal temperature difference between the inlet of the fixed bed and the outlet of the fixed bed of said reactor is less than 20° C.

The value of the longitudinal temperature difference is considered as an absolute value.

According to one preferred embodiment, the temperature at the inlet of the fixed bed of said reactor is between 330° C. and 360° C. and the longitudinal temperature difference between the inlet of the fixed bed of said reactor and the outlet of the fixed bed of said reactor is less than 20° C.

According to one preferred embodiment, in step ii), the HF/starting compounds molar ratio is adjusted so as to keep the longitudinal temperature difference between the inlet of the fixed bed and the outlet of the fixed bed of the reactor less than 20° C.

According to one preferred embodiment, in step ii), the HF/starting compounds molar ratio is greater than or equal to 5, advantageously greater than or equal to 10, preferably greater than or equal to 12.

According to one preferred embodiment, said reactor comprises side walls comprising an inner layer, an intermediate layer placed on said inner layer and an insulating layer placed on said intermediate layer; and the radial temperature difference between a point located at the center of the fixed bed of said reactor and a point located in the radial plane at the level of the inner layer of the side wall of said reactor is less than 10° C. Said inner layer is that which is in contact with the reagents. The value of the radial temperature difference is considered as an absolute value.

According to one preferred embodiment, said reactor comprises side walls comprising an inner layer, an intermediate layer placed on said inner layer and an insulating layer placed on said intermediate layer; said insulating layer being made of a heat-insulating material M2, the thickness of which ranges between 1 mm and 500 mm.

According to one preferred embodiment, the heat-insulating material M2 is selected from the group consisting of rock wool, glass wool, silicate fibers, calcium-magnesium silicates, calcium silicates, microporous insulators, cellular glass, expanded perlite and exfoliated vermiculite.

According to one preferred embodiment, the pressure at the inlet of said reactor is between 3 and 15 bara.

According to one preferred embodiment, the stream B comprises, apart from 2,3,3,3-tretrafluoropropene, HF, HCl, 2-chloro-3,3,3-trifluoropropene or unreacted 2,3-dichloro-1,1,1-trifluoropropane and 1,1,1,2,2-pentafluoropropane; and has an electrical conductivity of less than 15 mS/cm.

According to a second aspect, the present invention relates to a facility for producing 2,3,3,3-tetrafluoropropene, comprising:

an adiabatic reactor comprising a bottom, a cover and side walls joining the bottom and the cover, at least one fixed bed and at least one rod supporting one or more temperature sensor(s); said bottom, said cover and said side walls each comprise at least an inner layer, an intermediate layer placed on said inner layer and an insulating layer placed around said intermediate layer; said inner layer being made of a material M1 comprising a nickel mass content of at least 30°; said intermediate layer being made of a material M1' comprising at least 70° by weight of iron; said insulating layer being made of a heat-insulating material M2 selected from the group consisting of rock wool, glass wool, silicate fibers, calcium-magnesium silicates, calcium silicates, microporous insulators, cellular glass, expanded perlite and exfoliated vermiculite; the length of said at least one rod supporting one or more temperature sensor(s) being at least equal to the height of said fixed bed; and said at least one rod comprising at least one temperature sensor placed in said fixed bed;

a system for feeding said reactor with reaction stream comprising a supply line for hydrofluoric acid and at least one supply line for a stream A comprising 2-chloro-3,3,3-trifluoropropene or 2,3-dichloro-1,1,1-trifluoropropane;

a system for collecting and purifying the outlet stream from said reactor;

at least one conductivity meter capable of measuring the electrical conductivity of the reaction stream entering said reactor.

DETAILED DESCRIPTION OF THE INVENTION

The present invention relates to a process for producing 2,3,3,3-tetrafluoropropene. Preferably, said process for producing 2,3,3,3-tetrafluoropropene comprises the steps:

i) providing a stream A comprising at least one starting compound selected from the group consisting of 2-chloro-3,3,3-trifluoropropene and 2,3-dichloro-1,1,1-trifluoropropane; and ii) in an adiabatic reactor comprising a fixed bed composed of an inlet and an outlet, bringing said stream A into contact, in the presence or absence of a catalyst, with HF in order to produce a stream B comprising 2,3,3,3-tetrafluoropropene.

Preferably, the temperature at the inlet of the fixed bed of said reactor is between 300° C. and 400° C. and the longitudinal temperature difference between the inlet of the fixed bed and the outlet of the fixed bed of the reactor is less than 20° C.

Preferably, the temperature at the inlet of the fixed bed of said reactor is between 320° C. and 400° C., preferably between 320° C. and 375° C., more preferentially between 320° C. and 360° C., in particular between 330° C. and 360° C. In this step i), a temperature above 400° C. can render the catalyst irreversibly inactive, while a temperature below 300° C. prevents the fluorination reaction from being carried out.

Figure 2:
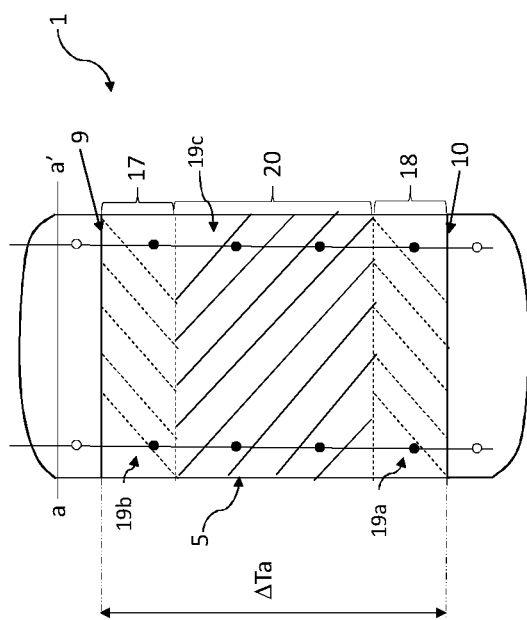
FIG. 2 schematically represents a view in longitudinal section of a reactor according to one particular embodiment of the present invention.

As mentioned above, in an adiabatic reactor, the temperature within the reactor, and in particular within the fixed bed, varies longitudinally, i.e. the temperature varies between the inlet of the reactor and the outlet of the reactor, in particular between the inlet of the fixed bed and the outlet of the fixed bed. FIG. 2 represents a schematic view in longitudinal section of a reactor 1 according to one particular embodiment of the present invention and comprising a fixed bed 5. The longitudinal temperature difference ΔTa is defined by the temperature difference between the inlet of the fixed bed 9 and the outlet of the fixed bed 10.

Preferably, the longitudinal temperature difference between the inlet of the fixed bed of said reactor and the outlet of the fixed bed of said reactor is less than 20° C., advantageously less than 19° C., preferably less than 18° C., more preferentially less than 17° C., in particular less than 16° C., more particularly less than 15° C., preferably less than 14° C., advantageously preferably less than 13° C., preferentially preferably less than 12° C., more preferentially preferably less than 11° C., particularly preferably less than 10° C.

According to a preferred embodiment, step ii) is carried out in the presence of a catalyst, preferably a chromium-based catalyst. Preferably, the chromium-based catalyst may be a chromium oxide (for example $CrO_2$, $CrO_3$ or $Cr_2O_3$), a chromium oxyfluoride or a chromium fluoride (for example $CrF_3$) or a mixture thereof. The chromium oxyfluoride may have a fluorine content of between 1° and 60° by weight on the basis of the total weight of the chromium oxyfluoride, advantageously between 5° and 55° by weight, preferably between 10° and 52° by weight, more preferentially between 15° and 52° by weight, in particular between 20° and 50° by weight, more particularly between 25° and 45° by weight, favorably between 30° and 45° by weight, more favorably from 35° to 45° by weight of fluorine on the basis of the total weight of chromium oxyfluoride. The catalyst can also comprise a cocatalyst chosen from the group consisting of Ni, Co, Zn, Mg, Mn, Fe, Zn, Ti, V, Zr, Mo, Ge, Sn, Pb and Sb; preferably Ni, Co, Zn, Mg and Mn; in particular Ni, Co and Zn. The content by weight of the cocatalyst is between 1° and 10° by weight, based on the total weight of the catalyst. The catalyst may or may not be supported. A support, such as alumina, for example in its a form, activated alumina, aluminum halides ($AlF_3$, for example), aluminum oxyhalides, activated carbon, magnesium fluoride or graphite, can be used.

Preferably, the catalyst can a specific surface area of between 1 and 100 $m^2/g$, preferably between 5 and 80 $m^2/g$, more preferentially between 5 and 70 $m^2/g$, ideally between 5 and 50 $m^2/g$, in particular between 10 and 50 $m^2/g$, more particularly between 15 and 45 $m^2/g$.

According to another preferred embodiment, step ii) is carried out in the absence of catalyst. In this case, said fixed bed contains an inert solid. The inert solid can be corundum, silicon carbide, quartz balls or rings, a metallic packing made of a metal M1 as defined in the present application or nickel balls. According to a preferred embodiment, step ii) is carried out at atmospheric pressure or at a pressure greater than atmospheric pressure, advantageously at a pressure of greater than 1.5 bara, preferably at a pressure of greater than 2.0 bara, in particular at a pressure of greater than 2.5 bara, more particularly at a pressure of greater than 3.0 bara. Preferably, step ii) is carried out at a pressure of between atmospheric pressure and 20 bara, preferably between 2 and 18 bara, more preferentially between 3 and 15 bara. Preferably, step ii) of the present process is performed with a contact time of between 1 and 100 seconds, preferably between 2 and 75 seconds, in particular between 3 and 50 seconds. An oxidant, such as oxygen or chlorine, may be added during step ii). The molar ratio of the oxidant to the hydrocarbon compound can be between 0.005 and 2, preferably between 0.01 and 1.5. The oxidant can be pure oxygen, air or a mixture of oxygen and nitrogen.

Preferably, in step ii), the HF/said starting compound molar ratio is greater than or equal to 5, advantageously greater than or equal to 10, preferably greater than or equal to 12. Advantageously, the HF/said starting compound molar ratio is between 12:1 and 150:1, preferably between 12:1 and 125:1, more preferably between 12:1 and 100:1.

As mentioned above, in an adiabatic reactor, the temperature within the reactor, and in particular within the fixed bed, varies radially, i.e. the temperature varies between the center of the reactor and the side walls of the reactor located in the same plane, in particular between the center of the fixed bed and the side wall of the reactor located in the same plane.

The control of the radial temperature in the fixed bed can be carried out by insulating the side walls of said reactor with a heat-insulating material of a defined thickness. Thus, said side walls each comprise at least one inner layer and an insulating layer placed around said inner layer. Preferably, an intermediate layer is placed between said inner layer and said insulating layer.

Figure 4:
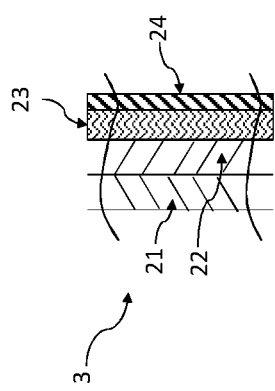
FIG. 4 schematically represents a sectional view of the side walls of a reactor according to one particular embodiment of the present invention.
Figure 3:
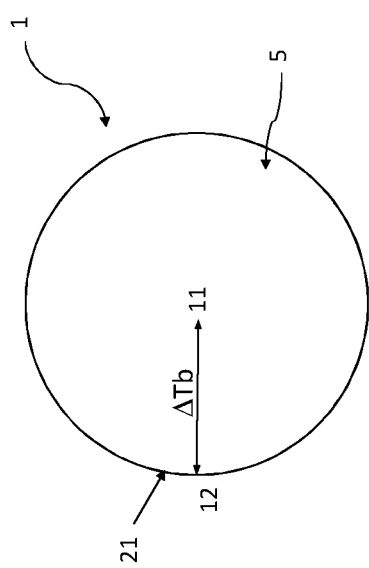
FIG. 3 schematically represents a view in transverse section of a reactor according to one particular embodiment of the present invention.

FIG. 3 represents a transverse view along the sectional plane (a,a') of a reactor 1 according to one embodiment of the present invention and comprising a fixed bed 5. The side walls 3 of said reactor comprise an inner layer 21, an intermediate layer 22 placed on said inner layer 21 and an insulating layer 23 placed on said intermediate layer 22 (FIG. 4). The radial temperature difference ΔTb is defined by the difference between a point located at the center of the fixed bed 5 of the reactor and a point 12 located in the radial plane at the level of the inner layer 21 of the side wall 3 of said reactor (FIG. 3).

Thus, the radial temperature difference between a point located at the center of the fixed bed of the reactor and a point located in the radial plane at the level of the inner layer of the side wall of said reactor is less than 10° C., advantageously less than 9° C., preferably less than 8° C., more preferentially less than 7° C., in particular less than 6° C., more particularly less than 5° C.

According to one preferred embodiment, said inner layer has a thickness of between 0.01 and 20 mm. Preferably, said inner layer can have a thickness of between 0.05 and 15 mm, preferably between 0.1 and 10 mm, more preferentially between 0.1 and 5 mm.

Said inner layer can be made of a material M1 comprising a nickel mass content of at least 30°. Advantageously, the material M1 comprises at least 40° by weight of nickel on the basis of the total weight of the material M1. Preferably, the material M1 comprises at least 45° by weight of nickel, more preferentially at least 50° by weight of nickel, in particular at least 55° by weight of nickel, more particularly at least 60° by weight of nickel, favorably at least 65° by weight of nickel, more favorably at least 70° by weight of nickel on the basis of the total weight of the material M1. The material M1 may also comprise chromium in a content of less than 35° by weight on the basis of the total weight of the material M1, advantageously less than 30° by weight, preferably less than 20° by weight, more preferentially less than 15° by weight, in particular less than 10° by weight, more particularly less than 5° by weight on the basis of the total weight of the material M1. The material M1 may also comprise molybdenum in a content of less than 35° by weight on the basis of the total weight of the material M1, advantageously less than 30° by weight, preferably less than 20° by weight, more preferentially less than 15° by weight, in particular less than 10° by weight, more particularly less than 5° by weight on the basis of the total weight of the material M1. Preferably, the material M1 comprises at least 40° by weight of nickel on the basis of the total weight of the material M1, preferably at least 45° by weight of nickel, more preferentially at least 50° by weight of nickel, in particular at least 55° by weight of nickel, more particularly at least 60° by weight of nickel, favorably at least 65° by weight of nickel, more favorably at least 70° by weight of nickel on the basis of the total weight of the material M1;

and less than 35° by weight of chromium, advantageously less than 30° by weight, preferably less than 20° by weight, more preferentially less than 15° by weight, in particular less than 10° by weight, more particularly less than 5° by weight of chromium on the basis of the total weight of the material M1; and less than 35° by weight of molybdenum, advantageously less than 30° by weight, preferably less than 20° by weight, more preferentially less than 15° by weight, in particular less than 10° by weight, more particularly less than 5° by weight of molybdenum on the basis of the total weight of the material M1. The material M1 may also comprise cobalt in a content of less than 10° by weight on the basis of the total weight of the material M1, advantageously less than 8° by weight, preferably less than 6° by weight, more preferentially less than 4° by weight, in particular less than 3° by weight, more particularly less than 2° by weight on the basis of the total weight of the material M1. The material M1 may also comprise tungsten in a content of less than 10° by weight on the basis of the total weight of the material M1, advantageously less than 9° by weight, preferably less than 8° by weight, more preferentially less than 7° by weight, in particular less than 6° by weight, more particularly less than 5° by weight on the basis of the total weight of the material M1. The material M1 may also comprise iron in a content of less than 25° by weight on the basis of the total weight of the material M1, advantageously less than 20° by weight, preferably less than 15° by weight, more preferentially less than 10° by weight, in particular less than 7° by weight, more particularly less than 5° by weight on the basis of the total weight of the material M1. The material M1 may also comprise manganese in a content of less than 5° by weight on the basis of the total weight of the alloy, advantageously less than 4° by weight, preferably less than 3° by weight, more preferentially less than 2° by weight, in particular less than 1° by weight, more particularly less than 0.5° by weight on the basis of the total weight of the material M1. The material M1 may also comprise copper in a content of less than 50° by weight, advantageously less than 45° by weight, preferably less than 40° by weight, more preferentially less than 35° by weight, in particular less than 30° by weight, more particularly less than 25° by weight of copper on the basis of the total weight of the material M1.

According to one preferred embodiment, said intermediate layer has a thickness of between 0.1 and 50 mm. Preferably, said intermediate layer may have a thickness of between 0.5 and 40 mm, preferably between 1 and 30 mm, more preferentially between 1 and 25 mm. According to one preferred embodiment, said intermediate layer 22 is placed between said inner layer 21, in contact with the reagents, and said insulating layer 23 (FIG. 4). Said intermediate layer 22 may be made of a material M1'. According to a preferred embodiment, the material M1' comprises at least 70° by weight of iron, advantageously at least 75° by weight, preferably at least 80° by weight, more preferentially at least 85° by weight, in particular at least 90° by weight, more particularly at least 95° by weight of iron on the basis of the total weight of the material M1'. The material M1' may also comprise less than 2° by weight of carbon, advantageously less than 1.5° by weight, preferably less than 1° by weight, more preferentially less than 0.75° by weight, in particular less than 0.5° by weight, more particularly less than 0.2° by weight, favorably less than 0.1° by weight on the basis of the total weight of the material M1'. More particularly, the material M1' may comprise between 0.01 and 0.2° by weight of carbon on the basis of the total weight of the material M1'. The material M1' may also comprise less than 2° by weight of molybdenum, advantageously less than 1.5° by weight, preferably less than 1.25° by weight, more preferentially less than 1° by weight of molybdenum on the basis of the total weight of the material M1'. More particularly, the material M1' may comprise between 0.1° and 1° by weight of molybdenum on the basis of the total weight of the material M1'. The material M1' may also comprise less than 5° by weight of chromium, advantageously less than 4° by weight, preferably less than 3° by weight, more preferentially less than 2° by weight, in particular less than 1° by weight of chromium on the basis of the total weight of the material M1'. More particularly, the material M1' may comprise between 0.5° and 2° by weight of chromium on the basis of the total weight of the material M1'. The material M1' may also comprise less than 2° by weight of silicon, advantageously less than 1.5° by weight, preferably less than 1.25° by weight, more preferentially less than 1° by weight of silicon on the basis of the total weight of the material M1'. More particularly, the material M1' may comprise between 0.1° and 1.5° by weight of silicon on the basis of the total weight of the material M1'. The material M1' may also comprise less than 2° by weight of manganese, advantageously less than 1.5° by weight, preferably less than 1.25° by weight, more preferentially less than 1° by weight of manganese on the basis of the total weight of the material M1'. More particularly, the material M1' may comprise between 0.1° and 1° by weight of manganese on the basis of the total weight of the material M1'.

Preferably, said insulating layer is made of a heat-insulating material M2. Said heat-insulating material M2 is selected from the group consisting of rock wool, glass wool, silicate fibers, calcium-magnesium silicates, calcium silicates, microporous insulators, cellular glass, expanded perlite and exfoliated vermiculite. The silicate fibers include, for example, aluminosilicate fibers. In particular, the side walls of said reactor comprise an insulating layer made of a heat-insulating material M2, the thickness of which ranges between 1 mm and 500 mm, preferably between 5 mm and 400 mm.

According to a preferred embodiment, the pressure at the inlet of said reactor is atmospheric pressure or a pressure greater than this; advantageously, the pressure at the inlet of said reactor is greater than 1.5 bara, preferably greater than 2.0 bara, in particular greater than 2.5 bara, more particularly greater than 3.0 bara. Preferably, step ii) is carried out at a pressure at the inlet of said reactor of between atmospheric pressure and 20 bara, preferably between 2 and 18 bara, more preferentially between 3 and 15 bara.

According to a preferred embodiment, the stream A comprises 2-chloro-3,3,3-trifluoropropene or 2,3-dichloro-1,1,1-trifluoropropane, HF and optionally 1,1,1,2,2-pentafluoropropane.

According to a preferred embodiment, the stream B comprises, apart from 2,3,3,3-tetrafluoropropene, HF, HCl, 2-chloro-3,3,3-trifluoropropene or unreacted 2,3-dichloro-1,1,1-trifluoropropane and optionally 1,1,1,2,2-pentafluoropropane.

According to a preferred embodiment, the stream B is purified, preferably by distillation, in order to form a first stream comprising 2,3,3,3-tetrafluoropropene, HCl and optionally 1,1,1,2,2-pentafluoropropane and a second stream comprising HF and 2-chloro-3,3,3-trifluoropropene or 2,3-dichloro-1,1,1-trifluoropropane.

Preferably, said stream B is distilled under conditions which are sufficient to form said first stream comprising 2,3,3,3-tetrafluoropropene, HCl and optionally 1,1,1,2,2- pentafluoropropane and said second stream comprising HF and 2-chloro-3,3,3-trifluoropropene.

In particular, the distillation can be carried out at a pressure of 2 to 6 bara, more particularly at a pressure of 3 to 5 bara. In particular, the temperature at the distillation column top is from −35° C. to 10° C., preferably from −20° C. to 0° C.

According to a preferred embodiment, said stream B obtained in step b) is cooled prior to the abovementioned purification. In particular, said stream B obtained in step b) is cooled to a temperature of less than 100° C., then distilled in order to form said first stream comprising 2,3,3,3-tetrafluoropropene, HCl and optionally 1,1,1,2,2-pentafluoropropane and said second stream comprising HF and 2-chloro-3,3,3-trifluoropropene or 2,3-dichloro-1,1,1-trifluoropropane; the temperature at the distillation column top is from −35° C. to 10° C. and the distillation is carried out at a pressure from 2 to 6 bara.

Said stream B can be cooled, before distillation, to a temperature of less than 95° C., advantageously of less than 90° C., preferably of less than 85° C., more preferentially of less than 80° C., in particular of less than 70° C., more particularly of less than 60° C., favorably of less than 55° C., advantageously favorably of less than 50° C., preferentially favorably of less than 40° C., more preferentially favorably of less than 30° C., particularly favorably of less than 25° C., more particularly favorably of less than 20° C. The cooling of the stream of products obtained to such temperatures can facilitate the subsequent distillation.

The cooling of said stream B can be carried out by virtue of one or a plurality of heat exchangers. The cooling of said stream B can be carried out by passing the latter through one, two, three, four, five, six, seven, eight, nine or ten heat exchangers; preferably, the number of heat exchangers is between 2 and 8, in particular between 3 and 7.

Said second stream comprising HF and 2-chloro-3,3,3-trifluoropropene or 2,3-dichloro-1,1,1-trifluoropropane can be recycled to step ii).

The first stream comprising 2,3,3,3-tetrafluoropropene, HCl and optionally 1,1,1,2,2-pentafluoropropane can be purified, preferably by distillation, so as to form a third stream, preferably at the top of the distillation column, comprising HCl and a fourth stream comprising 2,3,3,3-tetrafluoropropene and optionally 1,1,1,2,2-pentafluoropropane.

Preferably, the process according to the present invention is carried out continuously.

Preferably, the process is carried out continuously and in the gas phase.

Preferably, said stream A has an electrical conductivity of less than 15 mS/cm. Advantageously, the electrical conductivity of said stream A is less than 14 mS/cm, preferably less than 13 mS/cm, more preferentially less than 12 mS/cm, in particular less than 11 mS/cm, more particularly less than 10 mS/cm, more preferably less than 9 mS/cm, advantageously preferably less than 8 mS/cm, preferentially preferably less than 7 mS/cm, more preferentially preferably less than 6 mS/cm, particularly preferably less than 5 mS/cm. Preferably, step ii) is carried out in the presence of hydrofluoric acid having an electrical conductivity of less than 10 mS/cm, preferably less than 5 mS/cm. Preferably, said second stream that can be recycled to step ii) has an electrical conductivity of less than 15 mS/cm, advantageously less than 10 mS/cm, preferably less than 5 mS/cm.

The electrical conductivity of said stream A or of HF or of said second stream is measured prior to step i) or ii). Preferably, the electrical conductivity of the stream in question or of HF is measured when it is in liquid form. Said process according to the present invention can therefore comprise a step of heating the stream in question or HF prior to carrying out step i) or ii) so as to form said stream A and HF in gaseous form. Preferably, said stream A used in step i) is in gaseous form when it is brought into contact with HF. The electrical conductivity is measured at ambient temperature. The electrical conductivity is measured using an inductive conductivity measurement cell according to the practice known to those skilled in the art. Preferably, the measurement cell is coated with a material resistant to a corrosive medium, in particular resistant to hydrofluoric acid. The electrical conductivity of a stream can be reduced, in order to achieve a conductivity of less than 15 mS/cm, by reducing the concentration of electrolyte possibly present in the stream according to techniques known to those skilled in the art (distillation, cooling and separation by settling, passage through 3 to 5 Å molecular sieves or zeolites). Such an electrical conductivity makes it possible to improve the conversion and/or the selectivity of the reaction.

Figure 1:
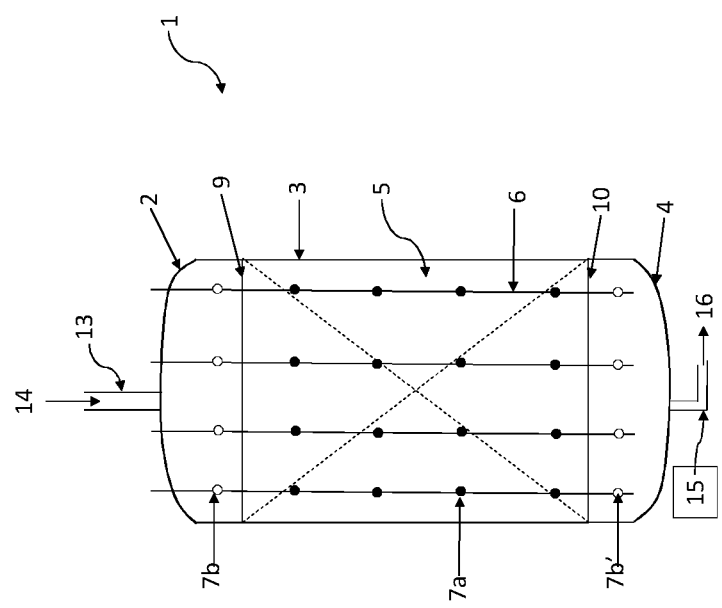
FIG. 1 schematically represents a reactor according to one particular embodiment of the present invention.

According to a second aspect of the present invention, an adiabatic reactor 1 is provided. Preferably, said reactor 1 comprises a bottom 4, a cover 2 and side walls 3 joining the bottom 4 and the cover 2, at least one fixed bed 5 and at least one rod 6 supporting one or more temperature sensors 7a, 7b (FIG. 1).

Preferably, said bottom 4, said cover 2 and said side walls 3 each comprise at least one inner layer 21, an intermediate layer 22 placed on said inner layer and an insulating layer 23 placed around said intermediate layer 22. Said inner layer 21, intermediate layer 22 and insulating layer 23 are respectively made of a material M1, M1' and M2 as described above.

According to one preferred embodiment, said insulating layer 23 may be covered by a base layer 24. Thus, said insulating layer 23 is placed between said intermediate layer 22 and said base layer 24 (FIG. 4). Said base layer 24 may be made of a material M3. Said material M3 can be a metallic coating made with sheets of aluminum, stainless steel or galvanized steel. Preferably, said base layer has a thickness of between 0.2 mm and 2 mm.

Said inner layer 21, said intermediate layer 22, said insulating layer 23 and said base layer 22 can be placed one on top of the other according to techniques well known to those skilled in the art.

Preferably, the length of said at least one rod 6 is at least equal to the height of said fixed bed 5. In particular, said at least one rod 6 comprises at least one temperature sensor, or at least two temperature sensors or at least 3 temperature sensors, advantageously at least 5 temperature sensors, preferably at least 7 temperature sensors, in particular at least 10 temperature sensors, preferably at least 12 temperature sensors, preferentially preferably at least 15 temperature sensors.

Preferably, at least one of said one or more temperature sensors, supported by said at least one rod, is placed in said fixed bed 5. In particular, at least two or three or four or five or six or seven temperature sensors, supported by said at least one rod, are arranged in said fixed bed 5.

Preferably, each rod 6 can comprise either an identical number or a different number of temperature sensors. In particular, each rod can comprise a temperature sensor in the headspace and/or in the bottom of the reactor (FIG. 1, reference 7b and 7b'). Likewise, the temperature sensors 7a, 7b can be distributed equidistantly or in a more targeted manner as required for controlling the temperature profile in the fixed bed.

Preferably, said reactor can comprise at least two rods 6, more preferentially at least three rods 6, in particular at least four rods 6. In particular, said reactor may comprise between 1 and 20 rods 6, advantageously between 2 and 15 rods 6, preferably between 3 and 10 rods 6.

Preferably, the reactor 1 is fed with hydrocarbon compound 14 via feed lines 13. The reactor also comprises effluent or outlet lines 15 for removing the reaction mixture 16 from the reactor (FIG. 1).

Preferably, the feed or outlet lines of the reactor are made of material capable of also resisting corrosion, for example made of the material M1 covered with a layer of material M2 and a base layer made of a material M3. The feed lines may be of tubular shape. Alternatively, the feed or outlet lines may comprise an inner layer, preferably made of a material M1 as described above, an insulating layer, preferably made of a material M2 as described above, and a base layer, preferably made of a material M3 as described above. The reactor also comprises one or more dephlegmator(s), one or more dip tube(s), one or more device(s) for introducing the raw materials, and one or more grating(s) for supporting and retaining the catalyst. Said one or more dephlegmator(s) and/or said one or more dip tube(s) and/or said one or more device(s) for introducing the raw materials and/or said one or more grating(s) for supporting and retaining the catalyst may comprise an inner layer, preferably made of a material M1 as described above.

Preferably, the fixed bed 5 comprises a catalyst or an inert solid or both. The inert solid can be corundum, silicon carbide, quartz balls or rings, a metallic packing made of a metal M1 as defined in the present application or nickel balls. Preferably, when the fixed bed 5 comprises a catalyst, the inert solid is placed on the upper part 17 and the lower part 18 of the fixed bed 5, said catalyst 19*c* being located between the layers of the inert solid 19*a* and 19*b*, in the central part 20 of the fixed bed 5. In an alternative embodiment, when the fixed bed 5 comprises a catalyst, the inert solid is placed in the upper part 17 or in the lower part 18 of the fixed bed 5. In an alternative embodiment, when the fixed bed 5 comprises a catalyst, no layer of inert solid is placed in the fixed bed. In an alternative embodiment, wherein the reactor does not contain a catalyst, the lower part 18, the central part 20 and the upper part 17 of the fixed bed 5 may contain only inert solid. This alternative embodiment can be implemented when, for example, step ii) of the process according to the present invention is carried out in the absence of a catalyst. In this case, the inert solid makes it possible to improve the distribution of gases inside the reactor. Preferably, the inert solid is corundum or nickel beads.

Preferably, the fixed bed 5 contains a catalyst layer 19*c* in its central part 20. In one preferred embodiment, the catalyst is distributed homogeneously in the fixed bed. The homogeneous distribution of the catalyst in the fixed bed makes it possible to minimize disruptions in the gas flow and to avoid hot spots within the catalyst layer. The presence of hot spots can lead to irreversible crystallization of the catalyst causing deactivation thereof. The loading of the fixed bed is carried out according to the specific method of dense loading of the catalyst. This method is known to those skilled in the art. It makes it possible to obtain an optimal distribution of the catalyst inside the reactor by avoiding channeling during the reaction and the attrition of the catalyst. In general, the apparent density by weight of the catalyst in the fixed bed is greater than the theoretical density by weight thereof. The apparent density by weight is determined according to ASTM D1895.

Preferably, said reactor is a gas-phase fluorination reactor.

The present invention makes it possible to implement a process for producing 2,3,3,3-tetrafluoropropene with a larger amount of catalyst, if said process is carried out in the presence of catalyst. In addition, the radial and longitudinal mastering and control of the temperature make it possible to maintain reaction conversion and selectivity.

According to a third aspect of the invention, a facility for producing 2,3,3,3-tetrafluoropropene is provided. Preferably, the facility comprises an adiabatic reactor according to the present invention, a system for feeding said reactor with reaction stream, a system for collecting and purifying the outlet stream from said reactor. Preferably, said facility also comprises at least one conductivity meter capable of measuring the electrical conductivity of the reaction stream entering said reactor.

Preferably, said facility also comprises a heat exchanger fed with the outlet stream and connected to a first distillation column. Preferably, said facility also comprises a compressor fed with the stream coming from said first distillation column. Preferably, said facility comprises a second distillation column fed with a stream coming from the compressor. Said second distillation column aims to remove all or a portion of the HCl present in the stream conveyed to it. Said facility may also comprise a plurality of other distillation columns for purifying the 2,3,3,3-tetrafluoropropene.

Figure 5:
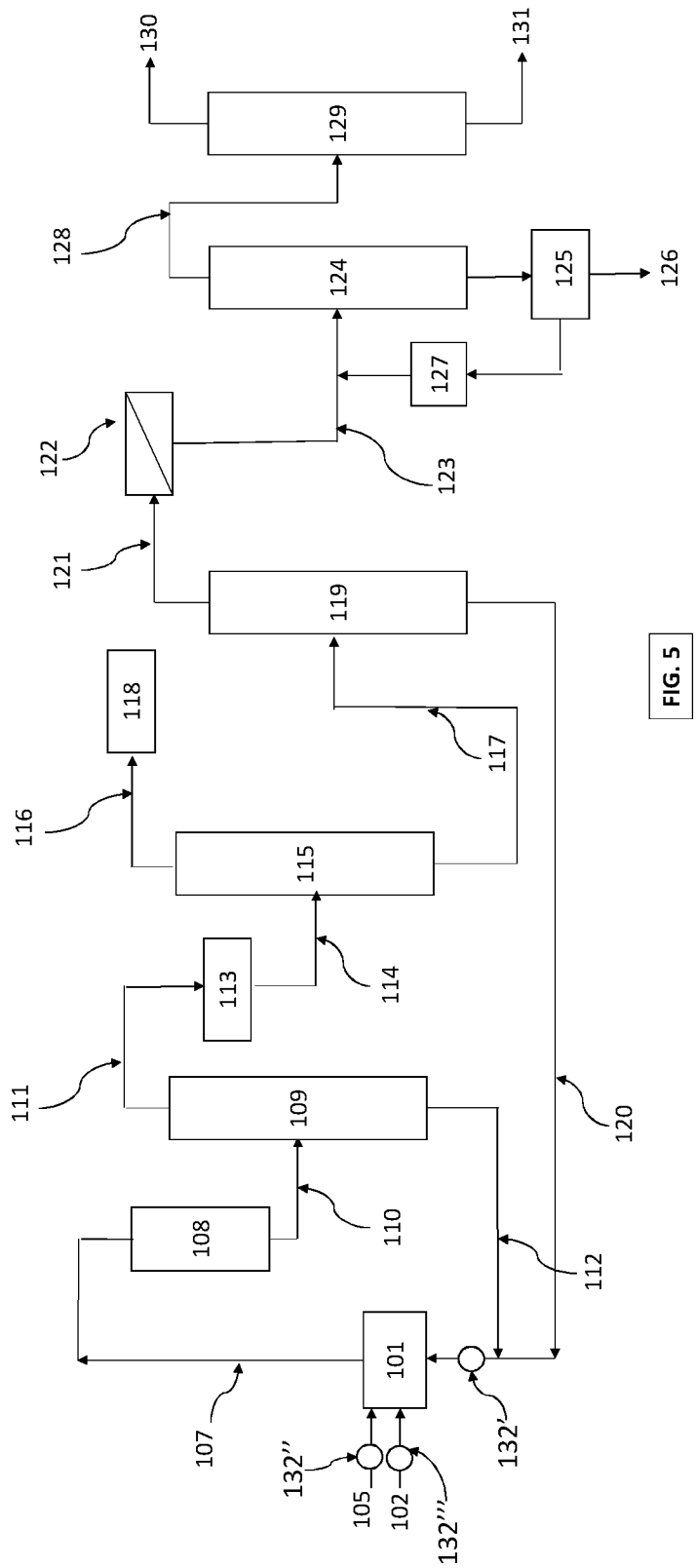
FIG. 5 schematically represents a facility for producing 2,3,3,3-tetrafluoropropene according to one particular embodiment of the present invention.

A facility according to one particular embodiment of the present invention is illustrated in FIG. 5. Preferably, the system for feeding the reactor 101 with reaction stream comprises a supply line for hydrofluoric acid 102 and a supply line for 2-chloro-3,3,3-trifluoropropene 105. The 2-chloro-3,3,3-trifluoropropene and HF can be mixed before bringing into contact with the catalyst in the reactor 101. Preferably, the outlet stream 107 comprises unreacted 2-chloro-3,3,3-trifluoropropene, HF, HCl, 2,3,3,3-tetrafluoropropene and optionally 1,1,1,2,2-pentafluoropropane. The facility comprises a heat exchanger 108 able to cool the outlet stream 107 coming from said reactor 101 to form a cooled stream. The outlet stream 107 is conveyed to a cooling device 108. The outlet stream 107 is thus cooled to a temperature of 0° C. to 70° C. before being introduced into a distillation column 109 via a pipe 110. The facility can therefore comprise a first distillation column 109 supplied with said cooled stream. The distillation column 109 is configured so as to allow separation between, on the one hand, hydrochloric acid and 2,3,3,3-tetrafluoropropene and optionally 1,1,1,2,2-pentafluoropropane and, on the other hand, hydrofluoric acid and 2-chloro-3,3,3-trifluoropropene. The stream of HF and of 2-chloro-3,3,3-trifluoropropene is recovered at the bottom of distillation column 109 and is recycled to the reactor 101 via the pipe 112. The stream comprising 2,3,3,3-tetrafluoropropene and hydrochloric acid and optionally 1,1,1,2,2-pentafluoropropane is recovered at the top of distillation column 109 to be conveyed via a pipe 111 to a compressor 113. According to a preferred embodiment, said facility comprises a compressor, preferably fed by the stream coming from the top of said first distillation column 109. The compressor makes it possible to compress the stream comprising 2,3,3,3-tetrafluoropropene and hydrochloric acid to a pressure of between 10 and 25 bara. The stream thus compressed is conveyed by the pipe 114 to a second distillation column 115. Said distillation column is configured so as to separate, on one hand, 2,3,3,3-tetrafluoropropene and optionally 1,1,1,2,2-pentafluoropropane and, on the other hand, hydrochloric acid. The hydrochloric acid is recovered at the top of the distillation column 115 to be conveyed to a purification device 118 by the pipe 116. The hydrochloric acid purification device 118 is a device known from the prior art, for example from WO 2015/079137. The 2,3,3,3-tetrafluoropropene and optionally 1,1,1,2,2-pentafluoropropane are recovered at the bottom of distillation column 115 to be conveyed via the pipe 117 to a third distillation column 119. The distillation column 119 is intended to separate the 2,3,3,3-tetrafluoropropene from the 1,1,1,2,2-pentafluoropropene possibly present in the outlet stream 107. The 2,3,3,3-tetrafluoropropene is recovered at the top of the distillation column to be conveyed to a purification device by the pipe 121. The 1,1,1,2,2-pentafluoropropene recovered at the bottom of the distillation column is recycled to the reactor 101 by the pipe 120. The purification device comprises in particular a device for removing the HF 122 and one or more distillation columns capable of purifying out of the stream comprising 2,3,3,3-tetrafluoropropene any impurities that it could contain, such as for example 1,1,1,2,2-pentafluoropropane and/or 1,3,3,3-tetrafluoropropene. The device for removing HF 122 can remove the residual HF which can be recycled to the reactor 101 (not shown). The device for removing HF 122 may be capable of allowing decanting of the HF or absorption of the HF. If the stream comprising 2,3,3,3-tetrafluoropropene contains impurities such as 1,3,3,3-tetrafluoropropene or 1,1,1,2,2-pentafluoropropane, said stream can be purified in the following manner, for example. The stream comprising 2,3,3,3-tetrafluoropropene is conveyed to a distillation column 124 by the pipe 123. The distillation column 124 is an extractive distillation column. An extraction agent 127 is added to the stream comprising 2,3,3,3-tetrafluoropropene. The extractive distillation column 124 makes it possible to remove any impurities possibly present in the stream comprising 2,3,3,3-tetrafluoropropene. These impurities can comprise 1,3,3,3-tetrafluoropropene. A stream comprising 2,3,3,3-tetrafluoropropene is recovered at the top of distillation column 124 and is conveyed by a pipe 128 to a distillation column 129. The distillation column 129 can make it possible to separate the 2,3,3,3-tetrafluoropropene from residual 1,1,1,2,2-pentafluoropropane. A stream 130 comprising 2,3,3,3-tetrafluoropropene is recovered at the top of the distillation column. A stream 131 comprising the residual 1,1,1,2,2-pentafluoropropane is recovered at the bottom of the distillation column; the latter being able to be recycled to the reactor 101. The stream 125 recovered at the bottom of the distillation column 124 comprises the organic extraction agent and the 1,3,3,3-tetrafluoropropene. These compounds are separated, for example by distillation, to form a stream 126 comprising 1,3,3,3-tetrafluoropropene. The organic extraction agent is for its part recycled to 127.

As mentioned above, the stream coming from the bottom of the distillation column 119 and the stream coming from the bottom of the distillation column 109 are conveyed to the reactor 101 respectively by the pipes 120 and 112. The two streams can be mixed before being introduced into said reactor 101. Furthermore, before being introduced into said reactor 101, the electrical conductivity of the two streams or of the mixture thereof is measured by the conductivity meter 132. The electrical conductivity of the HF and of the stream A can also be measured before they are introduced into the reactor 101.

The invention claimed is:

1. A process for producing 2,3,3,3-tetrafluoropropene, comprising the steps:
   i. providing a stream A comprising at least one starting compound selected from the group consisting of 2-chloro-3,3,3-trifluoropropene and 2,3-dichloro-1,1,1-trifluoropropane; and
   ii. in an adiabatic reactor comprising a fixed bed composed of an inlet and an outlet, bringing said stream A into contact, in the presence or absence of a catalyst, with HF in order to produce a stream B comprising 2,3,3,3-tetrafluoropropene,
   wherein the temperature at the inlet of the fixed bed of said adiabatic reactor is between 300° C. and 400° C. and a longitudinal temperature difference between the inlet of the fixed bed and the outlet of the fixed bed of said reactor is less than 20° C.

2. The process as claimed in claim 1, wherein the temperature at the inlet of the fixed bed of said reactor is between 330° C. and 360° C. and a longitudinal temperature difference between the inlet of the fixed bed of said reactor and the outlet of the fixed bed of said reactor is less than 20° C.

3. The process as claimed in claim 1, wherein, in step ii), the HF/at least one starting compound molar ratio is adjusted so as to keep a longitudinal temperature difference between the inlet of the fixed bed and the outlet of the fixed bed of the reactor less than 20° C.

4. The process as claimed in claim 1, wherein, in step ii), the HF/at least one starting compound molar ratio is greater than or equal to 5.

5. The process as claimed in claim 1, wherein said reactor comprises side walls comprising an inner layer, an intermediate layer placed on said inner layer and an insulating layer placed on said intermediate layer; and a radial temperature difference between a point located at a center of the fixed bed of said reactor and a point located in a radial plane at a level of the inner layer of the side wall of said reactor is less than 10° C.

6. The process as claimed in claim 1, wherein said reactor comprises side walls comprising an inner layer, an intermediate layer placed on said inner layer and an insulating layer placed on said intermediate layer; said insulating layer being made of a heat-insulating material M2, the thickness of which ranges between 1 mm and 500 mm.

7. The process as claimed in claim 6, wherein the heat-insulating material M2 is selected from the group consisting of rock wool, glass wool, silicate fibers, calcium-magnesium silicates, calcium silicates, microporous insulators, cellular glass, expanded perlite, and exfoliated vermiculite.

8. The process as claimed in claim 1, wherein the pressure at the inlet of said reactor is between 3 and 15 bara.

9. The process as claimed in claim 1, wherein the stream B comprises, apart from 2,3,3,3-tetrafluoropropene, HF, HCl, 2-chloro-3,3,3-trifluoropropene or unreacted 2,3-dichloro-1,1,1-trifluoropropane and 1,1,1,2,2-pentafluoropropane; and has an electrical conductivity of less than 15 mS/cm.

10. A facility for producing 2,3,3,3-tetrafluoropropene, comprising:
    an adiabatic reactor comprising a bottom, a cover and side walls joining the bottom and the cover, at least one fixed bed and at least one rod supporting one or more temperature sensor(s); said bottom, said cover and said side walls each comprise at least an inner layer, an intermediate layer placed on said inner layer and an insulating layer placed around said intermediate layer; said inner layer being made of a material M1 comprising a nickel mass content of at least 30%; said intermediate layer being made of a material M1' comprising at least 70% by weight of iron; said insulating layer being made of a heat-insulating material M2 selected from the group consisting of rock wool, glass wool, silicate fibers, calcium-magnesium silicates, calcium silicates, microporous insulators, cellular glass, expanded perlite and exfoliated vermiculite; the length of said at least one rod supporting the one or more temperature sensor(s) being at least equal to a height of said at least one fixed bed; and said at least one rod comprising at least one of the one or more temperature sensors placed in said fixed bed;

a system for feeding said reactor with a reaction stream comprising a supply line for hydrofluoric acid and at least one supply line for a stream A comprising 2-chloro-3,3,3-trifluoropropene or 2,3-dichloro-1,1,1-trifluoropropane;

a system for collecting and purifying an outlet stream from said reactor;

at least one conductivity meter capable of measuring the electrical conductivity of the reaction stream entering said reactor.

\* \* \* \* \*